US00PP10680P

United States Patent [19]

VandenBerg

[11] Patent Number: Plant 10,680

[45] Date of Patent: Nov. 10, 1998

[54] CHRYSANTHEMUM PLANT NAMED 'PLUM AKRON'

[75] Inventor: Cornelis P. VandenBerg, Salinas, Calif.

[73] Assignee: Yoder Brothers, Inc., Barberton, Ohio

[21] Appl. No.: 786,421

[22] Filed: Jan. 21, 1997

[51] Int. Cl.[6] ..... A01H 5/00

[52] U.S. Cl. ..... Plt./74.1

[58] Field of Search ..... Plt./74.1, 82.4, Plt./82.5

[56] References Cited

U.S. PATENT DOCUMENTS

| | | | |
|---|---|---|---|
| P.P. 7,325 | 9/1990 | VandenBerg | Plt./82.5 |
| P.P. 8,292 | 7/1993 | VandenBerg | Plt./74.1 |
| P.P. 9,105 | 4/1995 | VandenBerg | Plt./74.1 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding program with *Chrysanthamum morifolium",* Euphytica, 29:525–530.

Gosling, ed., 1979, "The Chrysanthemum Manual–6$^{th}$ edition", The National Chrysanthemum Society, London , Essex Telegraph Press, Ltd., pp. 329–336.

Broertjes, et al., 1978, "Application of Mutation Breeding Methods in the Improvement of Vegetatively Propagated Crops", Elsevier Sci. Publ. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in Chrysanthemum using x– and gamma radiation", Euphytica, 15:204–210.

UPOUROM–Plant Variety Database 1997/03, GTI Joule Retrieval Software, 'Plum Akron' citation.

*Primary Examiner*—Howard J. Locker

*Attorney, Agent, or Firm*—Foley & Lardner

[57] ABSTRACT

A Chrysanthemum plant named Plum Akron particularly characterized by its flat capitulum form; daisy capitulum type; red-purple ray floret color towards the red group; diameter across face of capitulum of 64 to 76 mm when fully opened, when grown as a pinched spray pot mum; photoperiodic flowering response of 50 to 56 days after start of short days; plant height, with 14 to 16 long days after sticking unrooted cuttings and with 1 to 2 applications of 2500 ppm B-9 SP ranges from 20 to 30 cm when grown as a pinched pot mum with 4 cuttings in a 15 cm pot; branching pattern is spreading and prolific, each plant developing 4 to 6 laterals after pinch; and recommended as a spray pot mum.

1 Drawing Sheet

The present invention comprises a new and distinct cultivar of Chrysanthemum, botanically known as *Dendranthema grandiflora,* and referred to by the cultivar name Plum Akron.

Plum Akron, identified as 4118 (91-413A05), is a product of a mutation induction program. The new cultivar was discovered and selected by inventor Cornelis P. VandenBerg on Jan. 25, 1994 in a controlled environment in Salinas, Calif. as one flowering plant within a flowering block established as rooted cuttings from stock plants which had been exposed as unrooted cuttings to an X-ray source of 1750 rads in Fort Myers, Fla. on Aug. 5, 1993. The irradiated parent cultivar was the cultivar Akron, disclosed in U.S. Plant Pat. No. 9,105, and described as a flat daisy spray pot mum with a red-purple ray floret color.

The irradiation program resulting in Plum Akron had as its primary objective the expansion of color ranges of the parent cultivar. The irradiation program comprised irradiation of cuttings of the parent cultivar at irradiation levels of 1500, 1750 and 2000 rads. A total of 2,113 cuttings harvested from a total of 225 irradiated plants were planted on Nov. 22, 1993. Of these, 12 initial selections were made, which selections were then revegetated and reflowered. Three consecutive flowerings resulted in discarding 9 of the original selections on Sep. 30, 1994. The 3 remaining selections were maintained as PIs (Possible Introductions) and further trialed in Salinas, Calif. and Leamington, Ontario, Canada, ultimately resulting in the decision to introduce one selection as Plum Akron, and one selection as Red Akron, the latter being disclosed in pending application Ser. No. 08/786,419 the one remaining selection was maintained for further trialing.

The first act of asexual reproduction of Plum Akron was accomplished when vegetative cuttings were taken from the initial selection in April of 1994 in a controlled environment in Salinas, Calif., by technicians working under supervision of Cornelis P. VandenBerg.

Horticultural examination of controlled flowerings of successive plantings has shown that the unique combination of characteristics as herein disclosed for Plum Akron are firmly fixed and are retained through successive generations of asexual reproduction.

Plum Akron has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Leamington, Ontario, Canada, under greenhouse conditions which approximate those generally used in commercial greenhouse practice.

The following traits have been repeatedly observed and are determined to be basic characteristics of Plum Akron, which, in combination, distinguish this Chrysanthemum as a new and distinct cultivar:

1. Flat capitulum form.
2. Daisy capitulum type.
3. Red-purple ray floret color towards the red group.
4. Diameter across face of capitulum of 64 to 76 mm when fully opened, when grown as a pinched spray pot mum.
5. Photoperiodic flowering response of 50 to 56 days after start of short days.
6. Plant height, with 14 to 16 long days after sticking unrooted cuttings and with 1 to 2 applications of 2500 ppm B-9 SP ranges from 20 to 30 cm when grown as a pinched pot mum with 4 cuttings in a 15 cm pot.

7. Branching pattern is spreading and prolific, each plant developing 4 to 6 laterals after pinch.

8. Recommended as a spray pot mum.

The accompanying photographic drawing is a side view of Plum Akron, grown as a spray pot mum with 4 cuttings in a 15 cm pot, with the colors being as nearly true as possible with illustrations of this type.

Of the commercial cultivars known to the inventor, the most similar in comparison to Plum Akron is the parent cultivar Akron. All traits of Plum Akron are similar to those of Akron, except for the ray floret color. The ray floret color of both Akron and Plum Akron are described as red-purple. However, the ray floret color of Plum Akron is significantly more red (R.H.S. 59C to 61A) than the ray floret color of Akron (R.H.S. 71B). Plum Akron also differs from sibling cultivar Red Akron only with respect to ray floret color, with the color of Plum Akron being red-purple compared to the deep red ray floret color of Red Akron.

In the following description color references are made to The Royal Horticultural Society Colour Chart. The color values were determined on plant material grown as a pinched pot mum with 4 cuttings in a 15 cm pot in Salinas, Calif., on Aug. 30, 1996.

Classification:

*Botanical.*—*Dendranthema grandiflora* cv Plum Akron.

*Commercial.*—Flat daisy spray pot mum.

Inflorescence

A. Capitulum:

*Form.*—Flat.

*Type.*—Daisy.

*Diameter across face.*—64 to 76 mm when fully opened.

B. Corolla of ray florets:

*Color* (*general tonality from a distance of three meters*) .—Red-purple towards the red group.

*Color* (*upper surface*).—Between 59C and 61A.

*Color* (*under surface*).—59C to 59D.

*Shape.*—Straight, flat, rounded ray floret tip.

C. Corolla of disc florets:

*Color* (*mature*).—14B.

*Color* (*immature*).—144A.

D. Reproductive organs:

*Androecium.*—Present on disc florets only; moderate pollen.

*Gynoecium.*—Present on both ray and disc florets.

Plant

A. General appearance:

*Height.*—20 to 30 cm when grown as a pinched pot mum with 14 to 16 long days after sticking unrooted cuttings prior to start of short days and with 1 to 2 applications of 2500 ppm B-9 SP.

*Branching pattern.*—Spreading and prolific, with 4 to 6 laterals developing after pinch.

B. Foliage:

*Color* (*upper surface*).—147A.

*Color* (*under surface*).147B

*Shape.*—Deeply lobed and strongly serrated.

What is claimed is:

1. A new and distinct Chrysanthemum plant named Plum Akron, as described and illustrated.

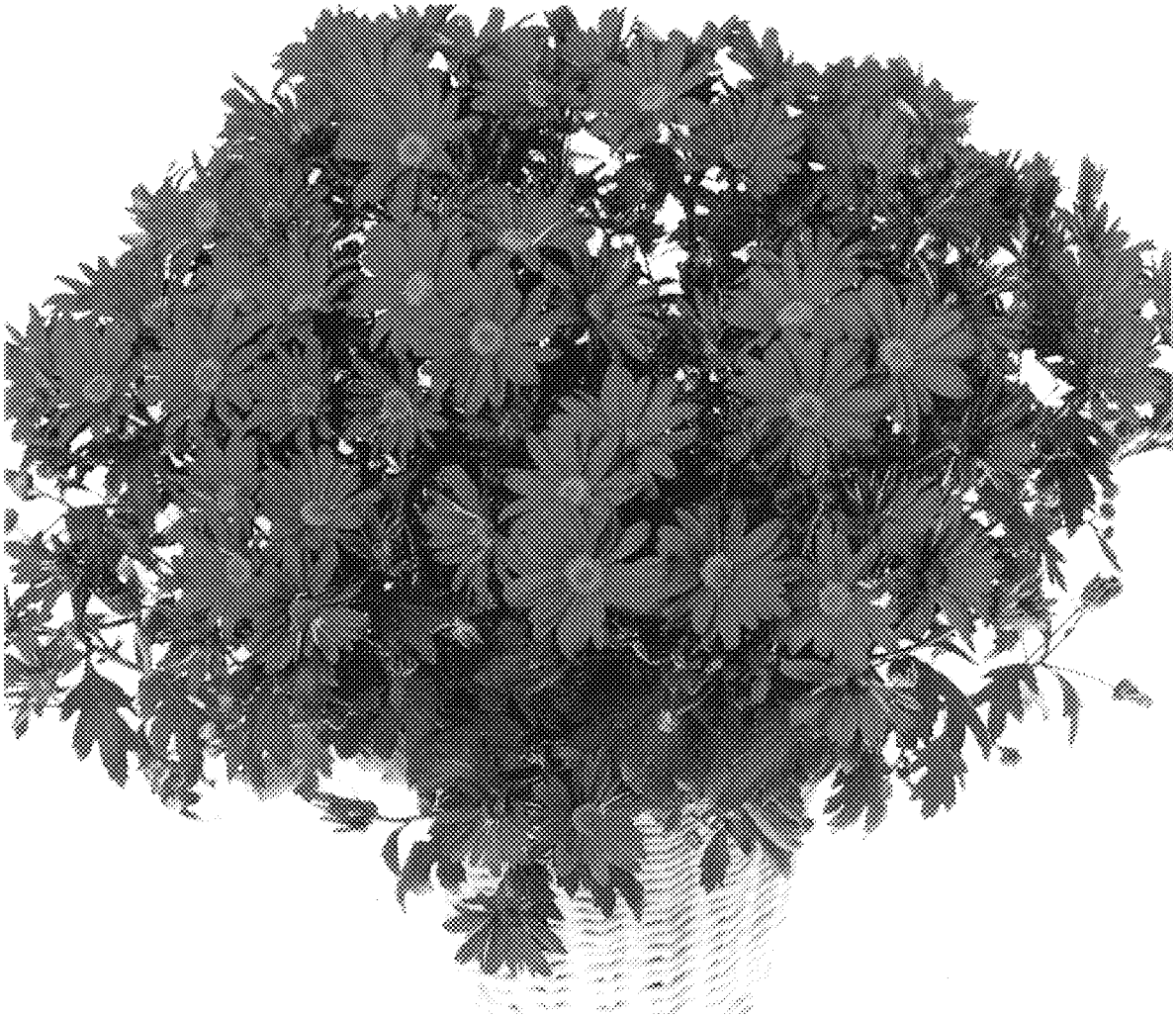

* * * * *